United States Patent [19]

Lloyd et al.

[11] Patent Number: 5,443,764
[45] Date of Patent: Aug. 22, 1995

[54] WATER-DISPERSIBLE GRANULES

[75] Inventors: John M. Lloyd, Richmond; Audrey G. Stuart, Nelson, both of New Zealand

[73] Assignee: ICI Australia Operations Propietary Limited, Melbourne, Australia

[21] Appl. No.: 321,411

[22] Filed: Oct. 11, 1994

Related U.S. Application Data

[63] Continuation of Ser. No. 144,610, Nov. 1, 1993, abandoned, which is a continuation of Ser. No. 967,547, Oct. 27, 1992, abandoned, which is a continuation of Ser. No. 746,807, Aug. 14, 1991, abandoned, which is a continuation of Ser. No. 327,983, filed as PCT/AU88/00201, Jun. 23, 1988, abandoned.

[30] Foreign Application Priority Data

Jul. 1, 1987 [NZ] New Zealand .................. 220920

[51] Int. Cl.$^6$ ............................................. B29B 9/00
[52] U.S. Cl. ........................................ 264/15; 264/140; 264/141; 71/64.08
[58] Field of Search ......................... 264/15, 140, 141; 71/64.08

[56] References Cited

U.S. PATENT DOCUMENTS

| Re. 27,214 | 11/1971 | Nakahara ................................ 264/15 |
| --- | --- | --- |
| 3,579,719 | 5/1971 | Moriya . |
| 3,627,865 | 12/1971 | Wittwer ................................ 264/118 |
| 3,758,679 | 9/1973 | Seidler ................................. 264/141 |
| 3,775,331 | 11/1973 | Borrello . |
| 4,036,227 | 7/1977 | Zaffaroni et al. ..................... 424/472 |
| 4,048,268 | 9/1977 | Ludwig ................................ 264/15 |
| 4,055,618 | 10/1977 | Fujita .................................. 264/141 |
| 4,082,532 | 4/1978 | Imof ........................................ 71/8 |
| 4,665,100 | 5/1987 | Ludwig ................................ 264/15 |
| 4,845,093 | 7/1989 | Haga et al. .......................... 514/247 |

FOREIGN PATENT DOCUMENTS

| 1022848 | 12/1977 | Canada . |
| --- | --- | --- |
| 1356105 | 4/1987 | France . |
| 220920 | 1/1989 | New Zealand . |
| 810290 | 3/1959 | United Kingdom . |
| 1433882 | 4/1976 | United Kingdom . |
| 2094624 | 9/1982 | United Kingdom . |
| WO8900079 | 1/1989 | WIPO . |

OTHER PUBLICATIONS

Pesticide Formulations.
Adjuvants for Herbicides.
Advances in Pesticide Formulation Technology, 1984.
Pesticide Formulations & Application Systems 3rd Symp, 1982.
Pesiticide Formulations & Application Systems 4th Symp, 1983.
Dry Application of Dry Flowable Formulations WA, Grandrud et al.
WDG & WDG Technology, H. T. Delli Colli, Westvaco Corp.
MIMS Annual 1986, pp. 8–53.
Preparation of Small Solid Pharmaceutical Spheres, Conine et al, D&CI, Apr. 1970.
Effect of Processing Variables in Particles Obtained by Extrusion, Woodruff et al, J. Pharm Sci vol. 61, No. 5, May 1972.
Tablet–Granulations Composed of Spherical–shaped Particles, Jalal et al, J. Pharm Sci, vol. 61, No. 9, Sep. 1972.
The Characterisation of Wet Powder Masses Suitable for Extrusion/Spheronization, Harrison et al, J. Pharm Pharmacol. 1985.

(List continued on next page.)

*Primary Examiner*—Mary Lynn Theisen
*Attorney, Agent, or Firm*—Cushman Darby & Cushman

[57] ABSTRACT

The invention relates to a process for the preparation of water-dispersible granules which comprises mixing the desired ingredients of the granules to form an extrudable composition, extruding the mixture, and rolling the extrusions to break them down into granules. The process of the invention is particularly suitable for the preparation of water-dispersible granules comprising agricultural chemicals (also known as dry flowables) as the process enables high production rates to be achieved and the products have high suspensibility and rapid dispersion.

17 Claims, No Drawings

WATER-DISPERSIBLE GRANULES

This is a continuation of application No. 08/144,610, filed on Nov. 1, 1993, which was abandoned upon the filing hereof and which is a continuation of Ser. No. 07/967,547, filed Oct. 27, 1992 as a continuation of Ser. No. 07/746,807, filed Aug. 14, 1991, as a continuation of Ser. No. 07/327,983, filed as PCT/AU88/00201, Jun. 23, 1988, all of the above applications now abandoned.

This invention relates to formulations of agricultural chemicals, minerals and other substances. It is more particularly concerned with the methods of preparing water dispersable granules containing such substances.

Agricultural chemicals are formulated in a number of ways, e.g. as large granules (prills) for direct application to soil, pasture or crops, emulsifiable concentrates, liquid flowable concentrates and wettable powders which are normally diluted with water for application. Liquid flowables and wettable powders comprise the majority of the agricultural chemical formulations sold throughout the world. The former are aqueous suspension and while generally giving satisfactory performance, can settle out of suspension during storage requiring vigorous mixing to re-suspend. Because of the high water content (generally around 50%), packaging and freight costs are increased.

Wettable powders are generally produced by first blending the technical grade chemical (which may already be in a finely divided state, e.g. in an air-milled form), with surfactants (wetting and dispersing agents), fillers and possibly other ingredients. The mixture is then passed through an air-mill or other suitable milling device to reduce the size of the additives (and technical chemical if not previously milled) as well as produce an intimate mixture of the components.

The resultant wettable powder is generally very bulky and becomes air borne readily. This can be hazardous to the user in the case of irritant or toxic materials.

The user of a wettable powder is generally required to observe the following procedures:

Carefully weigh the powder from a bulk container (often a dusty messy operation); disperse the powder in sufficient water to make a pourable concentrated suspension; transfer the concentrated suspension to water in an agitated spray tank, and then rinsing the suspension container thoroughly and finally clean up and decontaminate the scoops and balance pan, etc.

A relatively new concept is water dispersible granules (also known as dry flowables). These are granular formulations of agricultural chemicals that (when properly formulated), disperse readily in water and remain in suspension, i.e. perform as well as liquid flowables and wettable powders when prepared for spray application to soil or plants. This concept is being developed rapidly by agricultural chemical formulators especially in the U.S.A. and Europe. It is applicable generally to solid chemicals of low solubility as distinct from liquid or readily soluble chemicals. However, this invention also relates to dry flowable formulations of the latter type.

The usual method of producing "dry flowables" is to convert the technical chemical to a wettable powder type formulation in the first instance.

This involves blending and milling the ingredients of the formulation irrespective of whether the technical chemical has been previously milled, e.g. by air-milling.

The resultant powder is then converted to a granule by agglomeration using a pan-granulator or similar device using water or water containing an adhesive. This is a rather crude process and control of granule size is difficult to achieve. However, it seems to be the method most widely used at present.

This invention provides a method of producing water dispersible granules in which the granules are of a more uniform size than can be achieved by pan granulation.

This invention provides a process for forming water-dispersible granules comprising mixing the desired ingredients of the granules into an extrudable form, extruding the mix and then rolling the extrusions and optionally drying if required.

It is particularly preferred that the ingredients are mixed with water prior to extrusion and that the wet extrusions are rolled.

Accordingly, a particularly preferred embodiment of the invention provides a process for forming a water dispersible granule comprising mixing the desired ingredients of the granules in the presence of water to form an extrudable wet mix, extruding the wet mix, and rolling the wet extrusions to break down said extrusions to form granules, and optionally drying the granules.

In accordance with the invention it has surprisingly been found that extrusions which will have a diameter dependent upon the orifice in the extruder, but varying considerably in length, when rolled in a suitable rolling apparatus, break down into discrete sections which surprisingly are of a substantially uniform length.

The ingredients of the granule are first formed into extrudable form. The ingredients will generally comprise one of more active chemical components which may be liquid or solid at ambient temperature and either of an insoluble or water soluble type.

Typically the active chemical component comprises from 1 to 99% and preferably from 20 to 95% by weight of the dry weight of the composition.

The process of the invention may be performed using a wide range of active ingredients.

Examples of active ingredients include agricultural chemicals such as herbicides, fungicides, insecticides and fertilisers; pigments; dyestuffs; and trace elements.

Examples of herbicidal active ingredients may be selected from one or more of: benzo-2,1,3-thiadiazine-4-one-2,2-dioxides and such as bentazon; hormone herbicides such as MCPA, dichlorprop, MCPB and mecoprop; 3-[4-(4-halophenoxy)phenyl]-1,1-dialkylureas such as chloroxuron; dinitrophenols and their derivatives, for example, DNOC, dinoterb and dinoseb; dinitroaniline herbicides such as dinitramine, nitralin and trifluralin; phenylurea herbicides such as diuron and fluometuron; phenylcarbamoylphenylcarbamates such phenmedipham and desmedipham; 2-phenylpyridazin-3-ones such as as pyrazon; uracil herbicides such as lenacil, bromacil and terbacil; triazene herbicides such as atrazine, simazine and aziproptryne; 1-alkoxy-2-alkyl-3-phenylurea herbicides such as linuron, monolinuron and chlorobromuron; pyridine herbicides such as clopyralid and picloram; 1,2,4-triazin-5-one herbicides such as metamitron and metribuzin; benzoic acid herbicides such as 2,3,6-TBA, dicamba and chloramben; anilide herbicides such as balachlor, alachlor, propachlor and propanil; dihalobenzonitrile herbicides such as dichlobenil, bromoxynil and ioxynil; haloalkanoic herbicides such as dalapon and TCA; diphenylether herbicides such as fluorodifen and bifenox; N-(heteroarylaminocarbonyl)benzenesulphonamides such as DPX 4189; Aryloxyphen oxyprorionate herbicides such as fluazifop and diclofop; cyclohexane-1-3-dione derivatives such as alkoxydim-sodium and tralkoxydim; bipryidylium herbicides such as paraquat and diquat; organoarsenical herbicides such as MSMA; amino acid herbicides such as glyphosate; and other herbicides such as dipenamid and naptalam.

Preferred herbicides include diuron, atrazine, simazine, cyanazine, oryzalin, fluometuron, methazole, metoxuron and hexazinone.

Examples of fungicides include imazalil, benomyl, carbendazim (BCM), thiophanate-methyl, captafol, folpet, captan, sulphur, carbamates, dithiocarbamates, phenyl-tin compounds, carbathiins, dicarboximides (including iprodione, vinclozolin, procymidone), copper oxychloride, triforine, dodemorph, tridemorph, dithianon, pyrazophos, binapacryl, quinomethionate, panoctine, furalaxyl, aluminium tris(ethylphosphonate), cymoxanil, ethirimol, dimethirimol, fenarimol, fenpropidin, fenpropimorph, propiconazole, bupirimate, metalaxyl, ofurace, benalaxyl, oxadixyl, chlorothalonil, metaxanine, triazole derivatives such as triadimefon, triadimenol, diclobutrazol, flutriafol and penconazole and ergosterol-synthesis inhibiting fungicides.

Preferred fungicides for use as an active ingredient may include captan, thiram, mancozeb, dichlofluanid and metiram.

Examples of insecticides which may be used as an active ingredient may include pyrethroids such as cypermethrin organophosphorus insecticides, pirimor croneton, dimethoate, metasystox and formethion.

Examples of pigments may include any one of the wide range of powdered pigments or mixtures thereof. Suitable pigments may be chosen from diverse classes including: organic pigments of the anthraquinone, azoprophine, azo, dioxazine, naphthalene-tetracarboxylic acid, perylenetetracarboxylic acid, polycyclic, quinacridone and thioindigo series, specific examples of which may be found in the Colour Index, 2nd edition; and inorganic pigments such as the coloured pigments of the alkaline earth, antimony, cadmium, chromium, copper, iron, lead, ultramarine and zinc group (Kirk-Othmer, Encyclopedia of Chemical Technology 15, 496–516 (1968), white pigments such as titanium dioxide, zinc oxide, zinc white lithopones (Kirk-Othmer, Encyclopedia of Chemical Technology, 15, 517–541 (1968)); Copper phthalocyanine pigments such as those referred to in the Colour Index 2nd edition as Pigment Blue; and carbon black.

Examples of dyestuffs may include anthraquinone dyes, azo dyes, methine dyes and naphthoquinone dyes.

In addition to the active ingredient component the ingredients will normally include a surfactant component and optionally other components such as a filler component to provide the desired active ingredient content and/or a binding agent.

The term surfactant is used in the broad sense to include materials which may be referred to as emulsifying agents, dispersing agents and wetting agents and the surfactant component may comprise one or more surfactants selected from the anionic, cationic and nonionic type.

Examples of surfactants of the anionic type include soaps, salts of aliphitic monoesters or sulphuric acid such as sodium lauryl sulphate, salts of sulphonated aromatic compounds, for example sodium dodecylbenzenesulphonate, sodium, calcium or ammonium lignosulphonate or butylnaphthalene sulphonate, and a mixture of the sodium salts of diisopropyl- and triisopropylnapthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters with ethylene oxide and the lecithins and phosphoxylated surfactants such as phosphorylated ethylene oxide/propylene oxide block copolymer and ethyoxylated and phorphorylated stryryl substituted phenol.

Preferably the surfactant component will comprise at least one wetting agent such as those selected from alkyl naphthalene sulfonates, phosphate esters, sulphosuccinates and nonionics such as tridexyl alcohol ethoxylate; and/or at least one dispersing agent such as those selected from the group of napthalene condensates, lignosulfonates, polyacrylates and phosphate esters.

Typically the total surfactant component will comprise from 0.1 to 25% and preferably from 1 to 15% by weight of the dry weight of the composition.

A variety of fillers may be used in water dispersible granule compositions. Examples of fillers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, powdered magnesia, magnesium oxide, magnesium sulfate, sodium chloride, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Where used the filler component typically comprises from 1 to 99% and preferably from 5 to 80% by weight of the total granule composition. In one embodiment however, the granule composition may consist essentially of a filler type component such as one or more of talc, calcium carbonate and clays and a surfactant component. Such compositions may be of particular use in the paint industry for distributing fillers in aqueous suspension. In such cases the filler component may constitute up to 99% by weight of the granule composition. Optionally, a binding agent may also be incorporated in the granule composition. Suitable binding agents may include, for example, synthetic and natural gums, synthetic polymers such as poly vinyl acetate and cellulose derivatives such as methyl cellulose.

We have found that the rate of dispersion of water dispersible granule products is improved by wet-mixing the ingredients and preferably the mixing step is carried out to form an extrudable wet mix which has dough-like consistency, that is a consistency analogous to a stiff dough produced in the bread making process. Such a dough like consistency may be provided by thorough mixing or kneading using a mixing apparatus such as pug mill, double shafted auger or an extrusion apparatus may be adapted to provide suitable mixing.

The water is preferably present in the wet mixing step of the process in a controlled amount such that there is sufficient water to mobilise the surfactant component and enable the mixture to be formed into granules by extrusion but insufficient to cause the granules to stick together and agglomerate once formed. Although the quantity of water used in a given formulation will vary it will generally be in the range of from 5 to 50 liters (preferably from 10 to 30 liters) of water per 100 kg of dry mix.

The order of addition and mixing of the granule ingredients is not narrowly critical. In one embodiment, for example, the dry ingredients are blended and the composition is then mixed while water is added. The water may, for example be added as a fine spray and in one embodiment one of more surfactants are added as an aqueous solution to a dry mix of the other components. The use of the above described wet mixing process further has the advantage of allowing the use of solid technical grade surfactants without the need to finely grind such surfactants as is generally necessary in prior art processes.

Materials used in the process of the invention may be in a finely divided form, preferably in an air-milled form which is generally the form of technical grade chemicals supplied by manufacturers.

After thorough mixing or after otherwise putting the mix into a form suitable for extrusion, extrusion takes place through suitable orifices. The size of the granules will depend upon the size of the orifices and the extruder may thus be fitted with a mesh or die selected to provide a desired size of granule. Preferably extrusion orifices will be chosen to provide extrusions between 300 and 1000 microns in diameter. The extrusions can vary considerably in length, e.g. up to 8 cm or more long.

After extruding the wet mix the wet extrusions are broken down by rolling preferably in a tumbling action. In this specification the term rolling is used to mean causing the extrusions to roll or tumble against each other or a fixed or moving surface. The rolling motion causes the extrusions to break down into discrete sections of a length generally not exceeding three times their diameter. The rolling process also rounds off the granules to some extent. The rolling process may be carried out in numerous ways using a wide-range of apparatus. For example, on a small laboratory scale rolling may be carried out by shaking the extrusions in a suitable container. On a commercial scale rolling may be carried out, for example, in a rotating bowl apparatus, vibrating table apparatus or any suitable apparatus which causes the extrusions to break down into discrete sections which in turn are rounded to some extent by the rolling process.

Product recoveries where in excess of 95% by weight of product comprises particles within the preferred size range can generally be achieved using the process of the present invention without size screening. This is considerably greater than can be obtained when using a pan granulation method.

Preferably at least 95% by weight of the composition will comprise granules of size such that they pass through a 1700 micron sieve but are retained on a 300 micron sieve. In many cases it is possible to achieve over 99% of particles in this size range.

The rolling process may be done as a batch step or as part of continuous process in which extrusions are constantly fed from the extruder into the rolling apparatus and granular product is constantly delivered from the rolling apparatus.

It will be evident to those skilled in the art that one significant advantage of the process of the present invention is that the extrusions are not reduced (e.g. by cutting) to granules as they exit the extruder. This means that the rate of extrusion is not limited by the rate at which the extrusions can be broken down into granules and high extrusion rates can be used. This results in the process of the present invention being significantly more cost-effective than prior art extrusion processes for producing water dispersible granules.

The rate of processing of the extrusions will of course depend on many factors such as the consistency of extrusions, size of the rolling apparatus, rate of rotation and loading of the rolling apparatus. However, without undue experimentation a suitable product may be produced by rolling extrusions for periods in the range of from 30 seconds to 1 hour in the rolling apparatus although longer or shorter times may be used if desired. We have found it convenient to roll the extrusions for periods in the range of from 1 to 5 minutes.

The rate of rotation of the rolling apparatus is not narrowly critical. Preferred rotation rates are from 1 to 100 rpm and conveniently from 10 to 40 rpm.

The rolled granules are preferably dried. With some formulations the granules may be dried by allowing them to stand, however rapid or forced drying is generally preferred. Drying can, for example, be carried out by heating the granules on trays or in a fluidised bed dryer. The drying process will preferably remove as much water as possible in order to reduce weight and to provide good stability to the granules while still in a dry flowable state. Most preferably the granules will be dried to less than 0.5% as weight loss on complete drying.

The process of the invention considerably reduces the amount of oversized and undersized material which must be recycled. Fine particles and fragments which may be produced on extrusion are generally incorporated into the granules during tumbling. Consequently the granule composition is essentially dust free.

As granules may be prepared having uniform dimensions and density quantities for end use can be conveniently and accurately measured by volume. We have found that the granule composition produced by the above process have a lower tendency to powder and form dust than granules prepared by conventional processes such as pan-granulation while also having dispersibility properties which are typically superior.

The invention is now illustrated by but in no way limited to the following examples.

EXAMPLE 1

The following dry ingredients are weighed into a ribbon or other suitable blender fitted with a close fitting lid, and are blended for 30 seconds: 99.5% AI technical grade simazine in air milled form as supplied—90.453 kg. Fine Kaolin 'Koclay GM40' (filler-)—1.547 kg.

The following surfactant solution is then applied via a pressure vessel through spray nozzles mounted within the blender:

Morwet 'D-425' (dispersing agent) naphthalene formaldehyde condensate, sodium salt 6 kg; and Morwet 'EFW', (wetting agent) sulfated alkyl carboxylate and alkyl naphthalene sulfonate, sodium salt 1.5 kg, dissolved in 15 kg of water.

The wet mixture is blended for 2 minutes after this solution has been applied and is then transferred to a storage hopper fitted with a variable speed auger discharge.

The blended mixture is then extruded (manesty rotorgran) through a 30×31 g, 530 micron aperature mesh at a rate close to maximum machine load. This results in further intimate mixing of ingredients, formation of a dough and extrusion of same through the mesh.

The extrusions so formed are rolled in an open-mouth bowl for approx. 3 minutes during which time they break down into discrete granules and develop a reasonably smooth appearance. Granules are dried to a residual moisture content of 0.5% as loss on complete drying.

The dried product is screened and the very small amount of mainly undersized product so removed is returned to the primary blender for re-processing with a subsequent batch.

EXAMPLE 2

A commercially available water-dispersible granule formulation was obtained and found to have the following physical properties.

| Sieve analysis:- | |
| --- | --- |
| Retained on 300 microns | 10.1% |
| Retained on 150 microns | 70.76% |
| Retained on 106 microns | 87.17% |

The moisture content of the granules was 1.7%.

The granules were broken down and treated as follows:

The material from the commercially available granules was weighed and blended for 2 minutes with about 32% water (dry weight basis). The blended mixture was extruded (manesty rotogram) through a 744 micron screen of 94% open area (34 mesh, 30 gauge) and the extrusions rolled in an open-mouth bowl for approximately 3 minutes. The granules so produced were dried to a residual moisture content of about 0.5% as loss on complete drying. The suspensibility of the original commercial product was compared with the product reconstituted in accordance with the invention as described above.

| | Trial 1 | Trial 2 |
| --- | --- | --- |
| Commercial product | 72.35% | 71.64% |
| Reconstituted product | 97.61% | 99.03% |

The dispersion time of the formulations was found to be as follows:

| Commercial product | >1 minute |
| --- | --- |
| Reconstituted product | 30 seconds |

The above clearly demonstrates the advantage of the present invention in providing products of superior suspensibility and more rapid dispersion time when compared with products made by presently used granulation techniques.

EXAMPLE 3

The process of Example 1 was repeated using the following components expressed as weight percent based on product dried to 0.5% w/w water.

| Active Ingredient (AI) | 81.05 |
| --- | --- |
| Surfactant component: | |
| "Marasperse" N-22# | 8.0 |
| "Agrilan" DG 113* | 2.0 |

| -continued | |
| --- | --- |
| Kaolin clay | 8.45 |

A sodium lignosulphate dispersant ex Reed Lignin.
*A nonionic wetting agent supplied by Lankro Chemicals Limited.

The components were dry-mixed and then blended with water the total amount of water being controlled to provide a dough like consistency in the wet mixture prior to extrusion.

EXAMPLE 4

Compositions were prepared according to the procedure of Example 3 using the following active ingredient component with components used in the stated percent by weight of dry ingredients.

| Active Ingredient Component | |
| --- | --- |
| (a) Cypermethrin | 20–30% |
| (b) Diuron | 90% |
| (c) Simazine | 90% |
| (d) Atrazine | 90% |
| (e) Cyanazine | 90% |
| (f) Dalapon-Na | 80% |
| (g) Simazine | 15.3% |
| Amitrole | 5.3% |
| and Dalapon-Na | 20.8% |
| (h) Fluometuron | 80% |
| (i) Methazole | 80% |
| (j) Metoxuron | 80% |
| (k) Norflurazon | 80% |
| (l) Oryzalin | 85% |
| (m) Hexazinone | 85% |
| (n) Hexazinone and | 15% |
| Diuron | 50% |
| (o) Metribuzen | 75% |
| (p) Thiram | 80% |
| (q) Azinphos-methyl | 35%–50% |
| (r) Metiram and | 60% |
| Nitrothal-isopropyl | 12.5% |
| (s) Propargite | 30% |

We claim:

1. A process for the preparation of water dispersible granules comprising an active agricultural chemical for use in preparing aqueous dispersions suitable for application of the active agricultural chemical by spraying, the process comprising mixing the granule components, including the active agricultural chemical and a surfactant therefor, in the presence of water to form an extrudable wet mix, the amount of water being in the range of 5–50 liters per 100 Kg of the granule components, extruding the resulting wet mix to form a plurality of wet extrusions of a compactness such that on rolling the extrusions break down into discrete sections of substantially uniform length and then rolling the wet extrusions on each other or on a surface to break down said extrusions into said discrete sections, continuing the rolling action-so that said sections are rounded into granules of a length generally not exceeding three times their diameter and thereafter drying the granules thus obtained, the rolling being carried out in a rolling apparatus rotating at a speed in the range of from 1 to 100 rpm for a period of at least 30 seconds such that the resulting granules demonstrate more rapid dispersion and superior suspensability in water than obtainable with a corresponding composition using pan granulation, said granules being further characterized by their lower tendency to powder and form a dust than granules obtained by pan granulation.

2. A process according to claim 1 wherein the active ingredient component comprises in the range of from 1 to 99% of the dry weight of the composition and the surfactant component comprises from 0.1 to 20% by weight of the dry weight of the composition.

3. A process according to claim 1 wherein the ingredients include a filler present in an amount of 1 to 99% by weight of the total composition.

4. A process according to claim 1 wherein the active ingredient component comprises one or more materials selected from the group consisting of herbicides, fungicides, insecticides or fertilisers.

5. A process according to claim 1 wherein the active ingredient comprises at least one member of the group consisting of herbicides, fungicides and insecticides.

6. A process according to claim 1 wherein the ingredients are wet-mixed to form an extrudable wet mix of dough-like consistency.

7. A process according to claim 1 wherein the water is present in the wet mix in sufficient quantity to mobilise the surfactant component and enable granule formation by extrusion but insufficient to cause the granules to agglomerate once formed.

8. A process according to claim 1 where water is present in the wet mixing stage of the process in a ratio from 10 to 30 liters per 100 kg of dry mix.

9. A process according to claim 1 wherein in the extruding step comprises extruding the mix through orifices to provide extrusions of diameter in the range of between 300 and 1000 microns.

10. A process according to claim 1 wherein the rolling is carried out in a rotating bowl type apparatus.

11. A process according to claim 1 wherein at least 95% by weight of the granule composition comprises granules of size which pass through a 1700 micron sieve but are retained on a 300 micron sieve.

12. The process of claim 1 wherein the active ingredient is water-insoluble or of low water-solubility and the rolled granules are dried to a residual moisture content of 0.5% by weight or less.

13. A process according to claim 12 which comprises using a manesty rotogram as a low pressure extruder for the extruding step.

14. A process for preparation of water dispersible granules for the use in preparing aqueous dispersions of an active ingredient, the process comprising mixing the granule components, including the active ingredient and surfactant, in the presence of water to form an extrudable wet mix, the amount of water being in the range of 5–50 liters per 100 Kg of the granule components, extruding the resulting wet mix to form a plurality of wet extrusions of a compactness such that on rolling the extrusions break down into discrete sections of substantially uniform length and then rolling the wet extrusions on each other or on a surface to break down said extrusions into said discrete sections, continuing the rolling action so that said sections are rounded into granules of a size generally not exceeding three times their diameter and thereafter drying the granules thus obtained, the resulting granules demonstrating more rapid dispersion and superior suspensability in water than obtainable by a pan granulation process and being further characterized by their lower tendency to powder and form a dust than granules obtained by pan granulation.

15. A process for preparing an aqueous dispersion of an active ingredient which comprises adding the dispersible granules obtained by the process of claim 1 or claim 14 to water.

16. A process for preparing a sprayable aqueous dispersion of water dispersible granules comprising an agricultural chemical which comprises dispersing in water the water dispersible granules obtained by the process of claim 1.

17. In a process for applying an agricultural chemical by spraying an aqueous dispersion thereof, the improvement which comprises using, as the aqueous dispersion, an aqueous dispersion of water dispersible granules obtained by the process of claim 1.

* * * * *